(12) United States Patent
Rezac et al.

(10) Patent No.: US 8,159,662 B2
(45) Date of Patent: Apr. 17, 2012

(54) SYSTEMS AND METHODS FOR REMOTE UNMANNED RAMAN SPECTROSCOPY

(75) Inventors: Jeromy Paul Rezac, Albuquerque, NM (US); Howard N. LaValley, Albuquerque, NM (US); Noah Scott Higdon, Herndon, VA (US); Thomas Stewart McKechnie, Albuquerque, NM (US)

(73) Assignee: Exelis Inc., McLean, VA (US)

( * ) Notice: Subject to any disclaimer, the term of this patent is extended or adjusted under 35 U.S.C. 154(b) by 350 days.

(21) Appl. No.: 12/235,893

(22) Filed: Sep. 23, 2008

(65) Prior Publication Data

US 2010/0277723 A1    Nov. 4, 2010

Related U.S. Application Data (60) Provisional application No. 60/982,306, filed on Oct. 24, 2007.

(51) Int. Cl.
*G01J 3/44*    (2006.01)
(52) U.S. Cl. ...................................................... 356/301
(58) Field of Classification Search .......... 356/300–334, 356/609, 624
See application file for complete search history.

(56) References Cited

U.S. PATENT DOCUMENTS

| | | | |
|---|---|---|---|
| 6,487,440 B2 * | 11/2002 | Deckert et al. ................ 600/476 |
| 6,504,137 B1 * | 1/2003 | Reznichenko ............ 250/201.5 |
| 6,608,677 B1 | 8/2003 | Ray et al. |
| 6,996,292 B1 * | 2/2006 | Gentry et al. ................ 382/281 |
| 7,383,129 B1 | 6/2008 | Baillot et al. |
| 2003/0085334 A1 * | 5/2003 | Reznichenko et al. .... 250/201.5 |
| 2003/0184746 A1 * | 10/2003 | Johnsen et al. ............... 356/300 |
| 2007/0002319 A1 * | 1/2007 | Knopp et al. ................ 356/301 |
| 2007/0222981 A1 | 9/2007 | Ponsardin et al. |

FOREIGN PATENT DOCUMENTS

WO    2007032814 A2    3/2007

OTHER PUBLICATIONS

Mark D. Ray, Arthur J. Sedlacek and Ming Wu; Ultraviolet mini-Raman lidar for stand-off, in situ identification of chemical surface contaminants, Review of Scientific Instruments, AIP, Melville, NY, US, vol. 71, No. 9; pp. 3485-3489, Sep. 2000.

(Continued)

*Primary Examiner* — Tarifur Chowdhury
*Assistant Examiner* — Tara S Pajoohi
(74) *Attorney, Agent, or Firm* — Edell, Shapiro & Finnan, LLC (57) ABSTRACT

A Raman spectroscopy sensor integrated with an unmanned ground vehicle (UGV) includes a UGV having a robot arm and a camera mounted on the robot arm. A laser and telescope associated with a Raman sensor are mounted on the robot arm in such a way as to point in substantially the same direction in which the camera is pointed. A Raman spectral data acquisition and control module is mounted on the UGV and is configured to receive Raman spectral data from the telescope. A remote base station having a display and a data processing and analysis module is configured to receive data from the data acquisition and control module and to display for an operator images from the camera and information related to the Raman sensor. An autofocus system is preferably employed to automatically control telescope focus and thereby enable the Raman sensor to operate over a wide range, e.g., 0.5 m to 10 m.

13 Claims, 6 Drawing Sheets

OTHER PUBLICATIONS

J. Chance Carter, S. Michael Angel, McArion Lawrence-Snyder, John Scaffidi, Richard E. Whipple, and John G. Reynolds; Standoff Detection of High Explosive Materials at 50 Meters in Ambient Light Conditions Using a Small Raman Instrument, Applied Spectroscopy (online), vol. 59, No. 6, 2005 pp. 769-775.

Shiv K. Sharma, Anupam K. Misra, Bhavna Sharma; Portable remote Raman system for monitoring hydrocarbon, gas hydrates, and explosives in the environment, Spectrochimica Acta. Part A: Molecular and Biomolecularspectroscopy, Elsevier, Amsterdam, NL, vol. 61, No. 10, Aug. 1, 2005, pp. 2404-2412.

J. Chance Carter, Jon Scaffidi, Shana Burnett, Bryan Vasser, Shiv K. Sharma, S. Michael Angel; Stand-off Raman detection using dispersive and tunable filter based systems, Spectrochimica Acta. Part A: Molecular and Biomolecularspectroscopy, Elsevier, Amsterdam, NL, vol. 61, No. 10, Aug. 1, 2005, pp. 2288-2298.

S.K. Sharma, A.K. Misra, P.G. Lucey, S.M. Angel and C.P. McKay; Remote Pulsed Raman Spectroscopy of Inorganic and Organic Materials to a Radial Distance of 100 Meters, Applied Spectroscopy, (online), vol. 60, No. 8, 2006, pp. 871-876.

Alejandro Blanco, Leonardo C. Pacheco-Londono, Alvaro J. Pena-Quevedo and Samuel P. Hernadez-Rivera; UV Raman Detection of 2,4-DNT in contact with Sand Particles, Proc. Of Spie, (online), vol. 6217, 2006, pp. 621737-1-621737-10.

Charles W. Gardner, Rachel Wentworth, Patrick J. Treado, Parag Batavia, Gary Gilbert; Remote chemical biological and explosive agent detection using a robot-based Raman detector; Proc Spie (online), vol. 6962, Apr. 16, 2008, pp. 69620T-1-69620T-10.

* cited by examiner

SYSTEMS AND METHODS FOR REMOTE UNMANNED RAMAN SPECTROSCOPY

This application claims the benefit of U.S. Provisional Application No. 60/982,306 filed Oct. 24, 2007, which is herein incorporated by reference in its entirety.

FIELD OF THE INVENTION

The present invention is related to Raman spectroscopy, and more particularly to systems and methods for integrating Raman spectroscopy functionality with an unmanned ground vehicle, such as a robot.

BACKGROUND OF THE INVENTION

The danger of exposure to chemical or biological agents can be severe. Whether a result of unintended release, by way of, e.g., an accident, or intentional delivery, it is desirable to quickly and accurately identify (1) the type of agent that has been released and (2) the precise area of contamination. Early and accurate detection of such dangerous substances can be a significant factor in reducing potential casualties and limiting further spreading of the agent, e.g., by wind, human and animal contact, etc.

In recent years, there has been an increased interest in developing and deploying nuclear, biological, and chemical (NBC) sensor technologies to quickly identify unknown substances, contaminants, and agents, even at very low concentrations. Prior technologies designed to measure surface-deposited chemical contamination used vehicles and associated test equipment that retrieved a physical sample of the contaminant and then used an extremely cumbersome and time-consuming process based on a mechanical sampling wheel system to test for chemical agents.

In view of the complexity of such approaches, newer, simpler technologies were desired. One emerging technology in response to this desire is referred to, generally, as "standoff surface detection," and refers to a category of technologies that permit detection of a substance without actually having to physically come in contact with the substance. The goal of these detection systems is to provide the capability to detect, identify, locate, quantify, warn, and report chemical and biological threats and thereby give military forces or civilian personnel sufficient early warning to avoid (further) contamination.

One of the technologies that enables standoff surface detection is Raman spectrometry. Raman spectrometry is a technique used to characterize materials and thereafter to identify such materials. Typically, a laser transmitter serves as a spectrally narrow light source with high irradiance. The laser illuminates a known or an unknown substance, such as chemical compounds, biological agents, among others. A portion of the incident light is Raman scattered by the substance. This light is scattered in all spatial directions as well as shifted spectrally into several discrete wavelengths. These wavelength shifts correspond to unique vibrational energies associated with the molecular bonds in the substance.

In conventional Raman spectroscopy systems, the Raman scattered light is collected by a telescope and is coupled into a dispersive optical system. The telescope focuses the collected light onto, e.g., an optical fiber bundle. At the opposite end of the fiber bundle, individual fibers are oriented linearly to form an entrance slit for a grating-based spectrograph. An electro-optical detector array records the optical spectrum of the Raman scattered light. This spectrum serves as a "fingerprint" for the known or unknown substance. An analysis computer either stores the "fingerprint" along with information identifying the known substance, or more often, employs pattern-matching algorithms to identify the unknown substance from a spectral library of previously analyzed and "fingerprinted" substances.

Laboratory-based Raman spectrometry systems have been known for many years. Recently, portable Raman systems have become possible as a result of components that have decreased in size. A description of one such portable system can be found in U.S. Pat. No. 6,608,677, which is incorporated herein by reference. A backpack implemented man-portable Raman sensor has also recently been fielded by ITT (Wilmington, Del.). Aspects of that system are described in U.S. patent application Ser. No. 11/688,434, entitled Method, Apparatus and System for Rapid and Sensitive Standoff Detection of Surface Contaminants, and filed Mar. 20, 2007, which application is also incorporated herein by reference. Truck mounted Raman sensors have also been fielded to date. Reference may also be made to U.S. Pat. No. 6,788,407 for still further discussion of Raman spectrometry.

Notwithstanding these known systems, there remains a need to provide different forms of Raman sensors to meet the needs of both civilian and military personnel responsible for identifying and ultimately handling dangerous substances and items.

SUMMARY OF THE INVENTION

The present invention provides a unique implementation of a Raman spectroscopy sensor in which components of the system are mounted on, or, more preferably, closely integrated with, an unmanned ground vehicle (UGV) or robot that operates autonomously or that is controlled by a remote user. With this type of configuration, users of the Raman sensor can avoid having to be in the vicinity of dangerous substances or items. More particularly, with embodiments in accordance with the present invention, personnel are provided the capability to perform remote yet sensitive site exploitation including inspection of buildings, equipment, vehicles, aircraft, and other manmade or natural surfaces for the presence of unknown substances or items including, but not limited to, explosive material (e.g., TNT and RDX), homemade explosives and their precursors, and chemicals including chemical warfare agents (CWAs), and toxic industrial chemicals (TICs). One significant advantage of embodiments of the present invention is the ability to search for and detect improvised explosive devices (IEDs) without having to place people in the same location in which explosives might be hidden.

Other advantages of embodiments of the present invention include the fact that the technology (1) is non-contact (i.e., it is a standoff system), (2) allows mapping of the surface contamination, and (3) provides quick response (typically only seconds to perform detection).

In an embodiment, the present invention provides a UGV that includes a robot arm that may be steerable on its own or by way of steering the UGV itself. The UGV is preferably remotely controlled through a radio frequency (RF) link. The robot arm preferably includes a camera, and images from the camera are preferably streamed (over the RF link) back to a control station from which an operator can control the UGV. In this way, the operator can appropriately steer the UGV and point the camera towards targets of interest.

In addition to the foregoing, the UGV preferably also includes components of a Raman sensor. Specifically, along with the camera on the robot arm, there is preferably mounted a laser and associated telescope. As mentioned, in Raman spectroscopy the laser irradiates a desired location and the telescope gathers Raman scattered spectra. These spectra, in accordance with the present invention, are passed through an umbilical that includes, e.g., a bundle of optical fibers, to a sensor that is on board the UGV. The sensor may include a spectograph, a data acquisition and control module, a power conditioning module and an RF module that may be the same as an RF module that controls the UGV, or a separate RF module that is dedicated to controlling and communicating with the Raman sensor components.

A base station is preferably also provided for a remote operator to monitor and control the Raman sensor aspects of the UGV. In this regard, the base station preferably includes a data processing and analysis module and a display, such as a touch-screen display to facilitate operation of the system. The base station may be integrated with the control station of the UGV or may be separate. Indeed, it is contemplated that the operator of the UGV may not be the same operator of the Raman sensor. In this regard, the two separate operators need not even be in the same location.

In a preferred embodiment, an automatic telescope focusing mechanism is implemented that operates effectively even within constraints set by the limited space and weight allowance on the robot arm.

In still another possible embodiment, the Raman sensor components of the UGV are configured to be compatible with a man-portable/backpack version of a Raman sensor such that depending on the circumstances, e.g., nature of terrain or environment, perceived threat, etc., personnel may have the option of using a UGV or having personnel directly approach a target of interest.

The following is a list of the some preferred features of an embodiment of the present invention:

A compact remote sensor;
Warm up of less than 20 minutes;
Remotely adjustable standoff range (0.5 to 10 meters);
High flexibility in line-of-sight pointing direction using manual aiming or through the use of the UGV's remotely controlled arm;
Contamination mapping;
Radio Frequency (RF) link to a remoted (outside the area being surveyed) base station;
Rapid (<30 seconds) detection and identification of surface contaminants;
Simple, low-maintenance operation;
High selectivity/probability of detection with low false alarm rates;
Ruggedized for the operational environment; and
Capable of detecting and handling unknown substances.

These and other features of embodiments of the present invention and their attendant advantages will be more fully appreciated upon a reading for the following detailed description in conjunction with the associated drawings.

DETAILED DESCRIPTION

Figure 1:
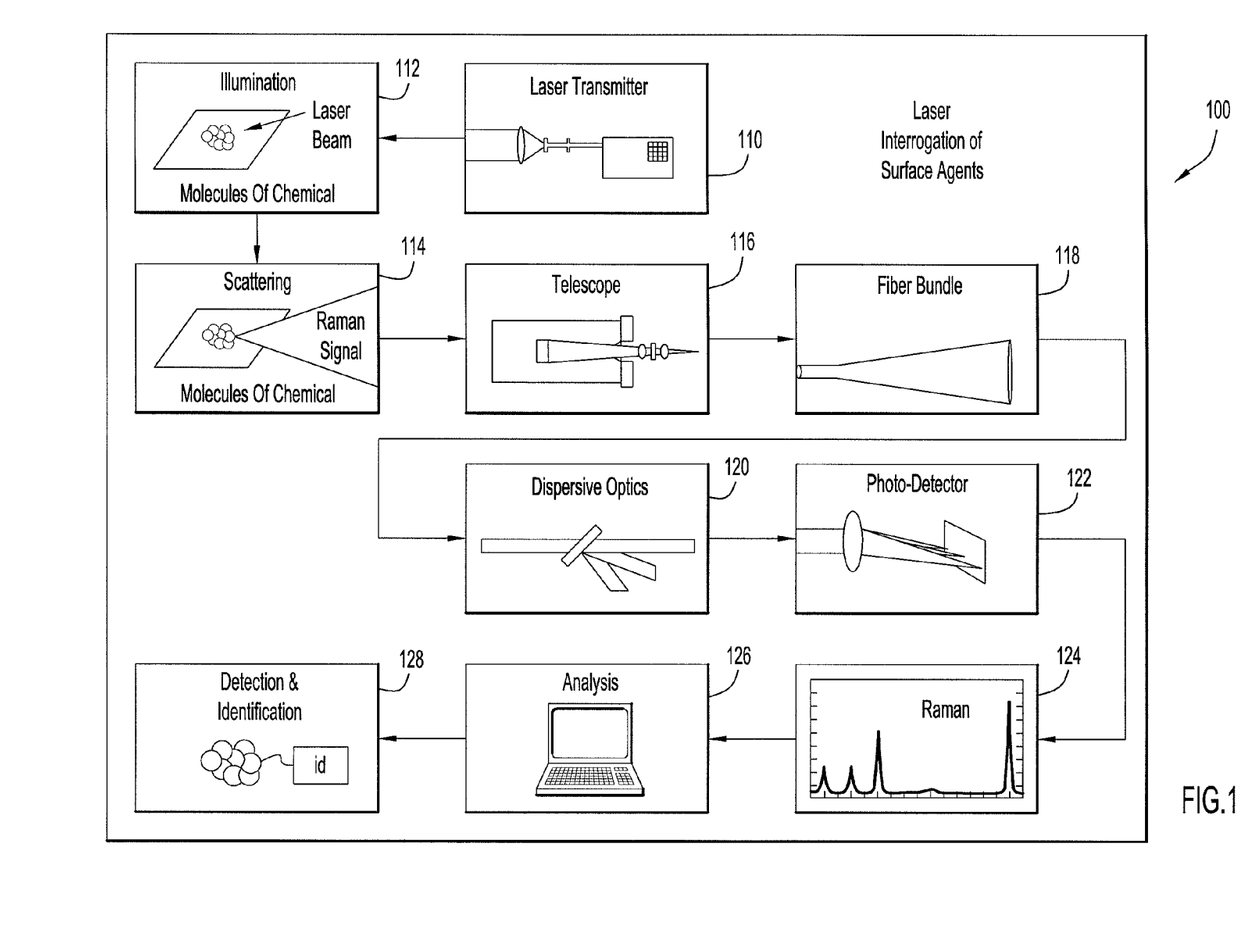
FIG. 1 is a schematic functional diagram of a Raman spectrometry system that may be employed with embodiments of the present invention.

FIG. 1 is a schematic functional diagram of a Raman spectrometry system 100 that may be employed with embodiments of the present invention. As shown, a laser transmitter 110 serves as a spectrally narrow light source with high irradiance. It illuminates a chemical agent deposited on a surface as indicted by functional block 112. A portion of the incident light is Raman scattered by the chemical compound, as indicated by functional block 114. This light is scattered in all spatial directions as well as shifted spectrally into several discrete wavelengths. These wavelength shifts correspond to the unique vibrational energies associated with the molecular bonds in the given chemical.

The Raman scattered light is collected by a telescope, block 116, and is coupled into a dispersive optical system. More specifically, a telescope focuses the collected light onto an optical fiber bundle 118. At the opposite end of the fiber bundle, individual fibers are oriented linearly to form an entrance slit for a grating-based spectrograph 120. An electro-optical detector array 122 (including, for example, an intensified charge coupled device (ICCD)) records the optical spectrum of the Raman scattered light 124. This spectrum serves as a "fingerprint" for the chemical compound. An analysis computer 126 employs pattern-matching algorithms to identify the chemical from a spectral library of known compounds, and ultimately identifies a specific compound 128.

Detection of explosive materials, in particular, has become increasingly important in recent years. Both civilian and military authorities have a great need to quickly identify explosive devices so that appropriate alerts, evacuations, defusing or eradicating efforts can get under way.

In this regard, it has recently been determined that the use of UV laser excitation maximizes the efficiency of Raman scattering from explosive chemicals. Techniques such as Laser Induced Breakdown Spectroscopy (LIBS) are not as selective or as mature a technology as Raman spectroscopy, while others like Laser Induced Fluorescence (LIF) are not as specific, and even limited, in that some explosive materials are non-fluorescing. The principal advantage of UV Raman spectroscopy over conventional visible-excitation Raman spectroscopy is sensitivity. UV excitation wavelengths intrinsically scatter more strongly than visible wavelengths. Moreover, many explosive chemicals strongly absorb UV radiation, and this increases the Raman scattering efficiency by many orders of magnitude through an effect called resonance enhancement. Resonance enhancement is particularly strong for chemical functionalities such as aromatic rings and nitro groups, both of which are common features of explosive compounds. Ultimately, the strength of the collected UV-Raman signal depends on several factors, including target concentration, wavelength-dependent absorption, and scattering properties of the target. The relationship between these parameters is discussed in more detail below using the explosive material TNT as an example.

Figure 2:
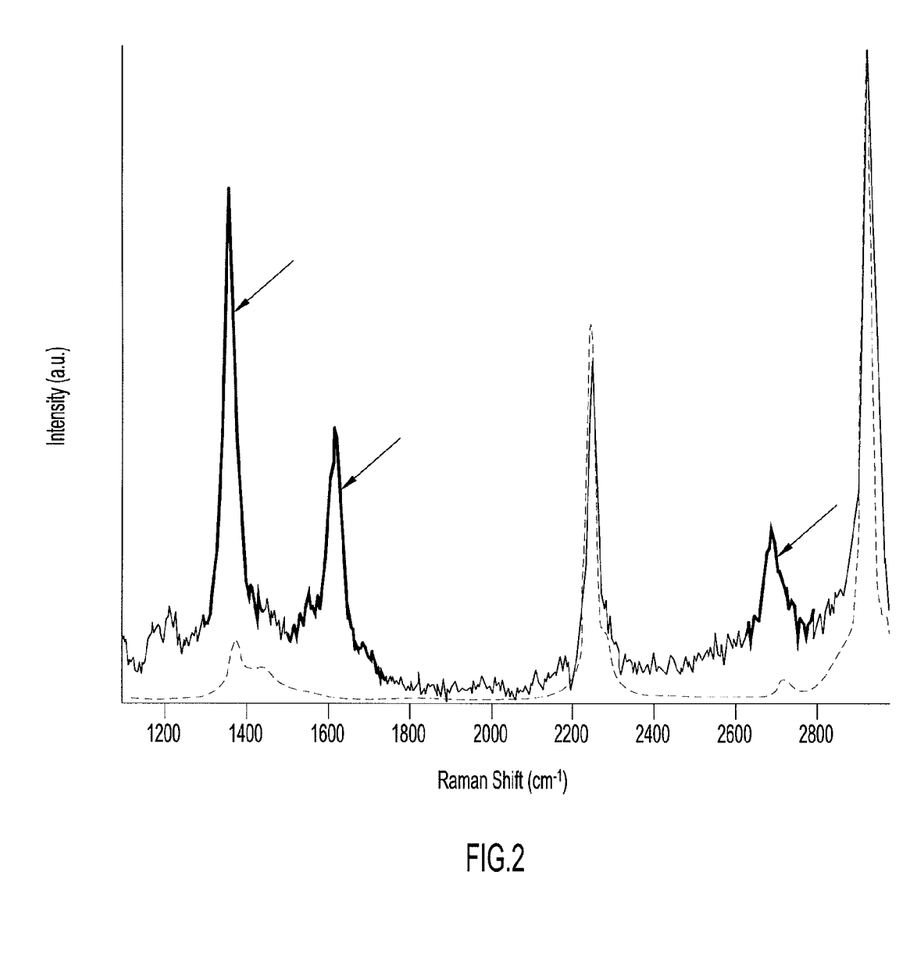
FIGS. 2 and 3 are graphs of Raman spectra for the explosive TNT.

A detailed analysis of the UV-Raman spectra for several samples of TNT indicate that the Raman scattering efficiency for 262-nm (UV) laser excitation is ~105 times greater than found for conventional 532-nm (Green) excitation, which is indicative of strong resonance enhancement. Shown in FIG. 2 is the 262-nm Raman spectrum for an 11 mM solution of military-grade TNT in acetonitrile. At this concentration, the acetonitrile molecules outnumber the TNT molecules ~1800:

1, yet the Raman bands of TNT (solid trace) carry intensities that are comparable to those belonging to acetonitrile (dotted trace). Clearly, scattering from TNT is strongly enhanced with 262-nm excitation. By comparison to the known 262-nm scattering cross section for acetonitrile, it has been has determined that the 262-nm scattering cross section for TNT is $3\times10^{-25}$ cm$^2$/molecule. In contrast, the 532-nm Raman spectrum of the same sample yields no detectable TNT Raman bands, which is consistent with the much weaker scattering expected at this wavelength (~$1\times10^{-30}$ cm$^2$/molecule or 300,000 times weaker). Notably, the 11-mM concentration and 1 mm path length used for this sample is equivalent to a TNT film 1.5 um thick, suggesting that thin films of explosive materials are best measured with UV Raman.

The strongly enhanced Raman signals provided by 262-nm laser excitation provides the sensitivity needed to detect and identify TNT at trace contamination levels. Strong absorption at 262 nm limits the number of molecules that contribute to the measured Raman signal to those found in the first 90-nm layer of TNT, regardless of sample thickness. The fact that the 11-mM solution described above and a bulk solid sample of TNT yield comparable signal levels validates the claim that absorption limits the 'interaction depth', which is defined herein as the sample thickness that yields 90% of the collected return signal expected from an infinitely thick sample. The key point is that the majority of the collected signal, like that shown in FIG. 2, is obtainable from an extremely thin film of TNT (<100 nm).

Figure 3:
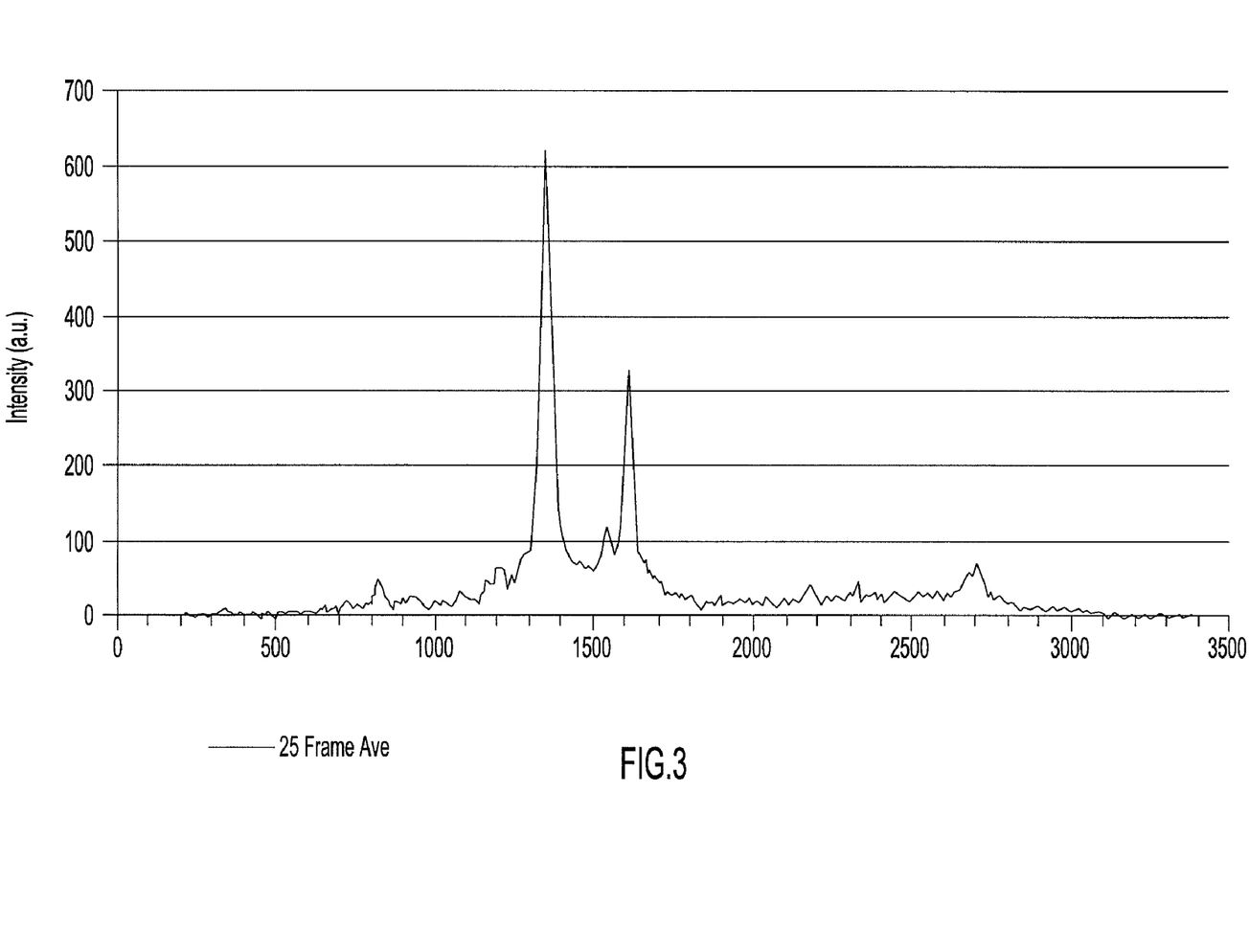

Recently, Lincoln Laboratory reported that explosive chemicals can be found at concentrations exceeding 20 ug/cm$^2$ on the exterior surfaces of vehicles that come into contact with the hands and feet of individuals who are involved with explosives, e.g., IEDs. Based on these findings, Lincoln Laboratory concluded that a UV Raman spectrometer equipped with a 1-W laser operating at 266-nm and a 30-cm collection aperture would be incapable of collecting Raman photons at detectable levels, even at standoff distances below 10 m. However, since UV-Raman scattering cross sections for TNT were not available at the time of publishing, the authors used a value of $1\times10^{-30}$ cm$^2$/molecule. Importantly, the authors recognized that strong resonance enhancement may in fact overcome the poor performance predicted by their model. The data in FIG. 2 indicate that the scattering cross section at 266 nm is indeed several orders of magnitude greater (~$1\times10^{-25}$ cm$^2$/molecule), which confirms their hypothesis regarding the impact of strong resonance enhancement on performance: the Raman spectrometer described by Lincoln Laboratory would in fact collect ~105 Raman photons/second at a standoff distance of 5 m, which is significantly more than originally predicted. Notably, a 4 cm$^2$ print with an evenly distributed TNT mass loading of 20 ug/cm$^2$ is ~30 nm thick, which is comparable in magnitude to the interaction depth for TNT at 262 nm. This suggests that the UV-Raman technology employed in the instant invention is well suited for detecting TNT at the contamination levels found on vehicle exteriors as reported by Lincoln Laboratory. In fact, TNT detection capabilities with UV-Raman spectroscopy have already been confirmed. FIG. 3 shows the 262-nm Raman spectrum of TNT recorded with a Raman spectrometer employed by embodiments of the present invention. The data in FIG. 3 were collected in one second at a standoff distance of one meter.

While TNT and other explosive materials detection using Raman spectroscopy is increasingly accurate, as described above, there remains a problem that personnel should preferably avoid being in the vicinity of explosives in the first place. Prior art stand off detection systems, including Raman sensors, require that personnel at least approach mysterious devices or surfaces that are to be analyzed. The present invention overcomes this potentially dangerous scenario by spatially separating the sensor from the operator.

Figure 4:
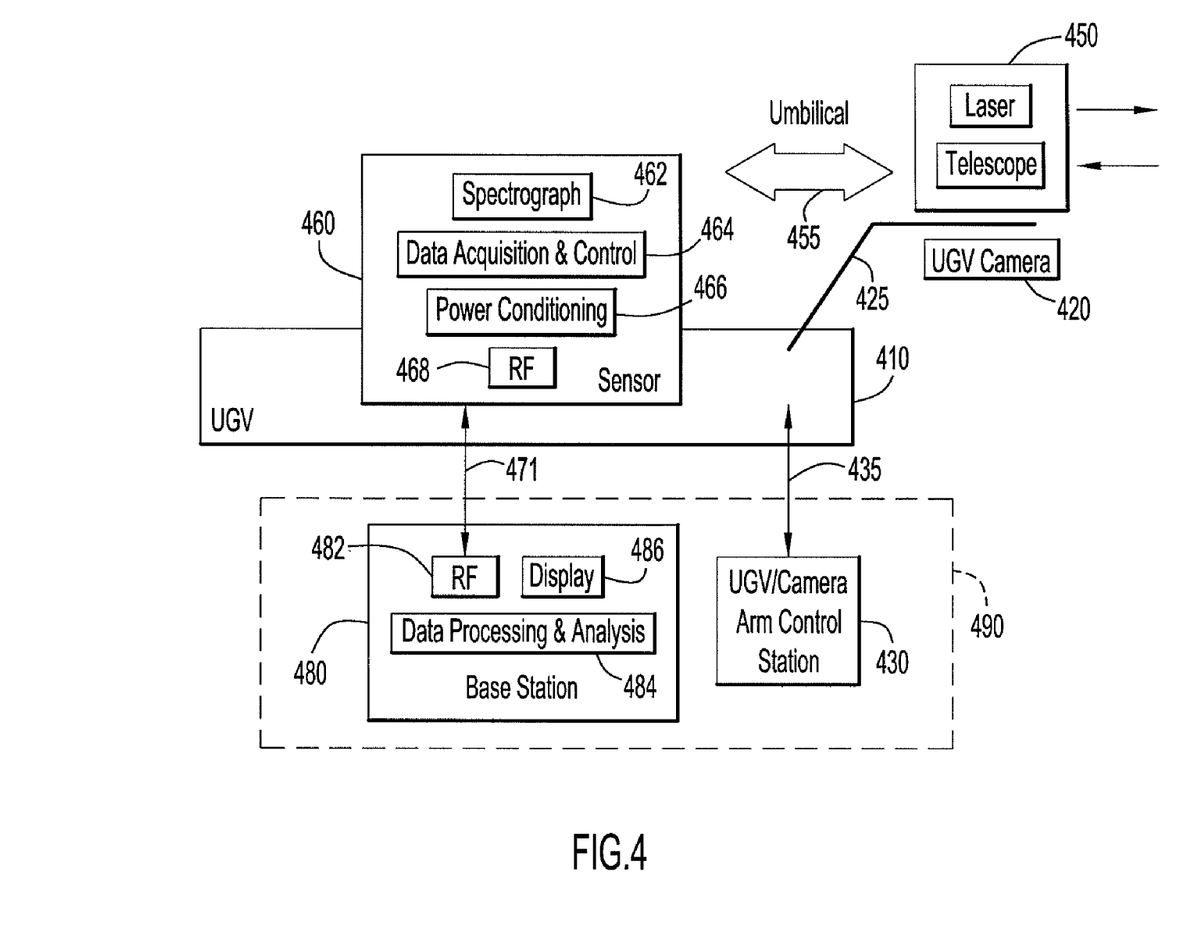
FIG. 4 shows, in block diagram form, an embodiment of the present invention.
Figure 5:
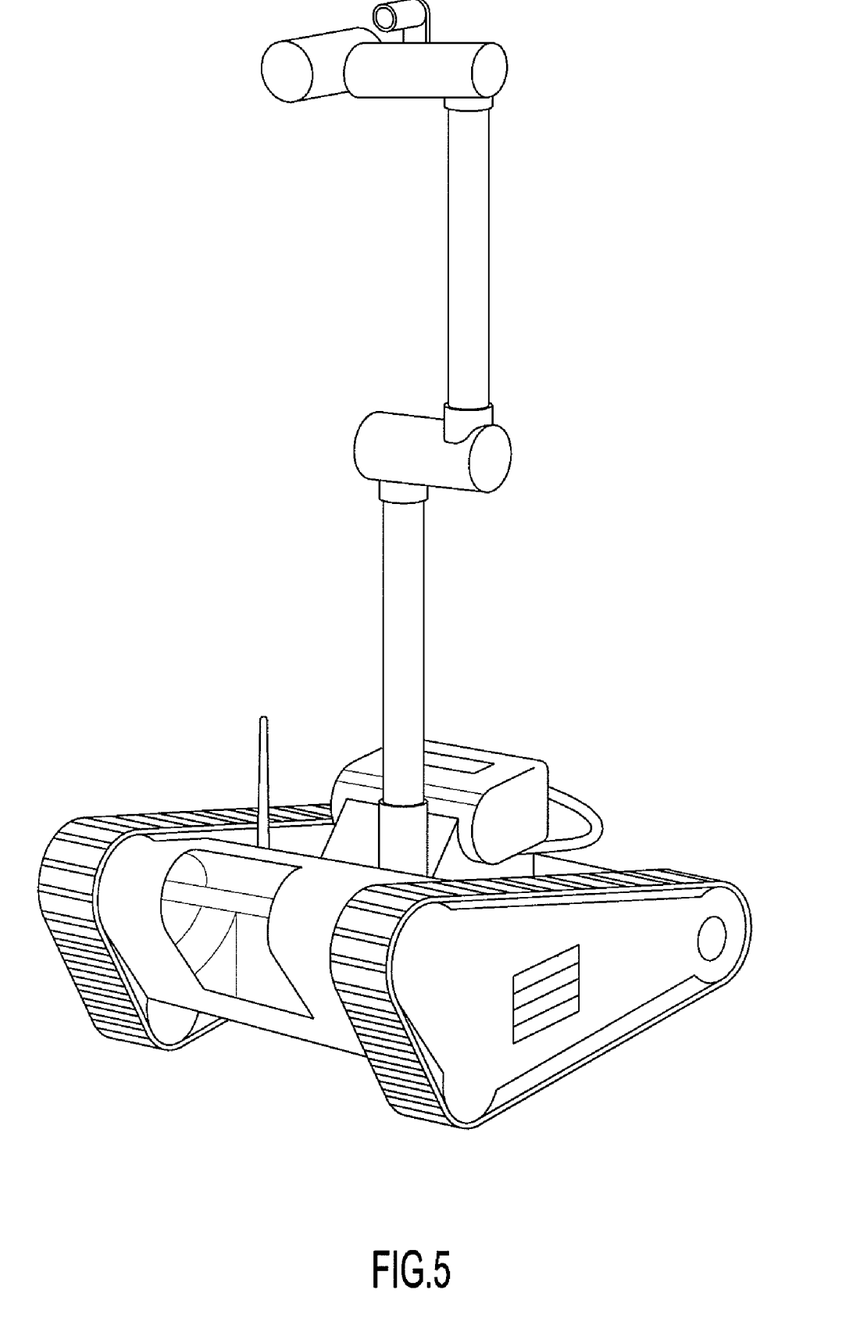
FIG. 5 depicts an unmanned ground vehicle with which the present invention may be integrated.

FIG. 4 shows, in block diagram form, an embodiment of the present invention. As shown, the system comprises an underlying unmanned ground vehicle (UGV) 410 including a UGV camera 420 mounted on an arm 425 extending from a body of the UGV 410 and a remote UGV/Camera Arm Control Station 430. UGV/Camera Arm Control Station 430 is preferably in communication with UGV 410 via a radio frequency (RF) link 435 and is operable to command UGV 410 and arm 425 to move in a selected direction, turn, stop, etc., all from a remote location. While such an RF link 435 provides the greatest degree of freedom for UGV 410 and an operator, it may be preferable under certain circumstances to have a wired connection between UGV 410 and UGV/Camera Arm Control Station 430. For example, a fiber optic wire may be used to remotely control UGV 410, arm 425 and camera 420, among other elements on UGV 410. One possible UGV that may be used in connection with the instant invention is the MATILDA II robotic platform shown in FIG. 5 and available from Mesa Robotics, Inc. (Madison, Ala.). Although not shown in FIG. 5, the MATILDA II robot also includes a remotely operated UGV/Camera Arm Control Station 430, which may be operated by an operator of the UGV.

Referring again to FIG. 4, integrated with UGV 410 in accordance with an embodiment of the present invention are components associated with a Raman spectrometer or sensor. These components include a Laser/Telescope module 450 that is mounted on the UGV itself, or more preferably, on the robot's arm 425 as shown. An umbilical (e.g., cable or collection of cables) 455 that comprises, for example, the fiber bundle described above, connects the Laser/Telescope module 450 to a Sensor module 460. Sensor module 460 comprises several components including a Spectograph 462 for receiving optical Raman spectra from the telescope of the Laser/Telescope module 450, a Data Acquisition & Control unit 464 that captures the spectral data using, e.g., an intensified charge coupled device (ICCD) camera, a power conditioning unit 466 for providing appropriate electrical power to the several components and modules associated with the Raman spectrometer and related equipment, and an RF unit 468 that is configured to wirelessly exchange communications with a base station 480.

Base station 480, itself, comprises an RF unit 482 that maintains wireless communications 471 with RF unit 468, a Data Processing & Analysis module 484 and a display 486. While Data Processing & Analysis module 484 is shown as being part of base station 480, the functionality of this module may likewise be located on UGV 410. The primary purpose of Data Processing & Analysis module 484 is to perform spectral pattern matching against a library of known Raman spectra, and attempt to identify a substance then being irradiated or that has been irradiated by the laser on the UGV 410. Display 486 may then alert an operator of the possible substance identification, and provide further information such as steps to take in light of the type of substance identified, or information about whom to contact to initiate remediation.

In accordance with one possible implementation, if a received spectral signal is a "persistent unknown" (e.g., it is not a member of the current library), the system provides the operator the options of: (1) adding the signature to the library as an important unknown, (2) ignoring the detected signature, or (3) postponing any decision until the next occurrence of the unknown. Information regarding received spectral information may be presented to an operator via display 486, and the operator may be requested to provide input to the system, via, e.g., a touch screen capabilities of display 486.

It is noted that FIG. 4 depicts UGV/Camera Arm Control Station 430 and base station 480 as separate components. However, it may be preferable that a single integrated control mechanism be implemented for the system to facilitate control thereof, e.g., using one set of controls, one display, etc. Such integrated control is designated by reference numeral 490. With one display, for example, an operator may be able to view precisely what the laser is interrogating. More specifically, images from UGV camera 420 may be streamed back to a display, which display is also operable to depict what the laser of Laser/Telescope module 450 is irradiating. Consequently, if, e.g., an explosive substance is identified, the operator can more easily identify the object on which the explosive material traces have been found, and thereby communicate that information to an explosives demolition expert. Such images may further be stored for later use, e.g., for training. Moreover, the display may show a real time video of where the robot is looking and include overlay or tiled views on the display showing the results of the Raman interrogation.

In an alternative embodiment, the UGV/Camera Arm Control Station 430 and the base station 480 are purposefully maintained as distinct functional units thereby allowing the possibility for different operators to operate respective components of the system, even when those operators are not in the same location.

The distance or range at which the Raman spectroscopy system on the UGV can practically detect substances is a factor in the configuration of the remote unmanned Raman spectroscopy system of the present invention. While a 20 mW laser is effective at 3 meters (with 1 second dwelling on a target) for detecting surface contaminants, it is preferable that the range of the system be more on the order of ten meters. Consequently, a more powerful laser is preferably used in order to ensure that sufficient laser power can be delivered to a selected target. In one possible implementation, a 500 mW 263 nm laser available from, e.g., Photonics Industries (Bohemia, N.Y.) may be employed to obtain the necessary power for increased range. Of course, other lasers and powers sufficient to deliver appropriate power to a target contaminant may also be used.

Additionally, for ranging of this magnitude (ten meters), the telescope component of the Laser/Telescope module 450 is preferably able to focus over a range of 0.5 to 10 meters. In one possible implementation, an electrically activated focusing mechanism can be used in conjunction with internal pointing diodes and the UGV's camera 420 to adjust focus remotely. That is, by monitoring a field of view of the UGV's camera 420, an operator can remotely focus the optical components of the Laser/Telescope module 450. Alternatively, an automatic focus (autofocus) system may be implemented to thereby relieve the operator of having to manually control telescope focus. This can save time, and increase accuracy of detection. A detailed discussion of an autofocus system that may be employed in connection with the instant invention is provided later herein.

In one possible implementation, the Raman spectroscopy components of the system may be modular components that can be shared with a man-portable version Raman sensor. A description of such a man-portable Raman detection system can be found in U.S. patent application Ser. No. 11/688,434, as mentioned previously. The man-portable detection system described therein includes a hand-held unit, a processing unit and an umbilical cable that connects the hand-held unit with the processing unit. In an embodiment described therein, at least portions of the processing unit are contained in a wearable backpack.

In accordance with embodiments of the instant invention, selected components of Raman spectroscopy system mounted or integrated with UGV 410 are modularized such that they can also be used with a man-portable Raman detection system. More specifically, the hand-held unit described in U.S. patent application Ser. No. 11/688,434 may be configured such that it has similar functionality to the Laser/Telescope module 450 shown in FIG. 4. Likewise, umbilical 455 of the present invention may be configured similarly to the umbilical cable described in U.S. patent application Ser. No. 11/688,434. Finally, sensor module 460 may be configured to have similar functionality to the processing unit described in U.S. patent application Ser. No. 11/688,434. Similar respective enclosures may also be provided for the several possibly modular components identified above. With such modularity, an overall system for detecting unknown substances might include a combination system that comprises both a UGV sensor and a man-portable sensor, wherein personnel in the field can easily select and enable either type of system (UGV or man-portable) depending on the perceived threat, or any other consideration.

In a preferred embodiment, components such as the Laser/Telescope module 450, umbilical 425 and Sensor module 460 are available to personnel as Line Replaceable Units (LRUs), thereby making field repairs relatively simple. Because components such as the Laser/Telescope module 450 and Sensor module 460 are likely to be exposed to the elements for significant amounts of time, enclosures for these components preferably have appropriate environmental seals (to guard against rain, decontamination spray booths, etc.), are EMI/EMC hardened (particularly for military applications), and have appropriate shock/vibration isolation.

Wireless link 471 may be a high bandwidth, spread spectrum RF data link. Wireless link 435 may also be integrated with wireless link 471, or may be a separately operated link (e.g., different frequency, different modulation technique, etc.).

Base station 480 may be a centralized device, and have the capability to monitor not just one UGV, but possibly multiple UGVs. When multiple UGVs are being used simultaneously and only one operator is available, then autonomous operation of the UGV may be preferable. In any event, an output of the base station 480 may also be connected via an electronic network, e.g., Ethernet (wired or RF), to a scene commander's workstation that integrates the activities of all fielded UGVs or man-portable devices.

Regarding UGV 410, it is preferable to employ a robot that is small enough to use inside buildings and tunnels while maximizing its payload. The MATILDA II robot identified above has a payload capacity on the order of 125 pounds and can operate for six hours on its batteries. The man-portable backpack and wand described in U.S. patent application Ser. No. 11/688,434 weigh about 46 pounds including a 1-hour battery. The robotic arm 425 of the MATILDA robot weighs about 45 pounds and has a payload capacity of about 35 pounds. The weight of Laser/Telescope module 450 is on the order of 5 to 20 pounds. Thus the robotic arm 425, Laser/Telescope module 450, and Sensor module 460 weigh less than 105 pounds, leaving 20 pounds for additional batteries.

The batteries may be standard military battery packs (e.g. 5590, 2590), or may be more advanced batteries with higher energy densities. Battery selection impacts the length of time the UGV 410 may be able to operate, but is otherwise not critical to the instant invention.

From the foregoing, those skilled in the art will appreciate that components of a Raman spectrometer mounted on or integrated with a UGV in accordance with the present invention yields a compact remote sensor with remotely adjustable standoff range of 0.5 to 10 meters, thus enabling operators to analyze a host surfaces in the vicinity of the UGV 410. In one implementation, the UGV arm 425 is used to aim the Laser/Telescope module 450. By capturing location data of the UGV and position data of the arm 425, such as by use of GPS and well-known position encoders, it is also possible to generate coordinates of individual suspect locations and devices, as well as to help generate a map of the extent of surface contamination or locations of potential explosive devices. Such maps or mapping data can be integrated with other geographical information systems that may further assist personnel in tracking and removing undesirable agents and devices.

In a preferred embodiment, and as mentioned, the UGV and Raman sensor are controlled remotely through an RF link to a remote site, thereby ensuring that personnel are not put in unnecessary danger. The operator may be at a nearby location, or may be located at a significantly distant location.

Also, because spectral pattern matching can be performed within seconds, it is possible to identify unknown agents within, typically, less than 30 seconds. This allows the UGV to make many hundred or even thousands of interrogations during the lifetime of a single set of batteries. The spectral data collected is also normally very unique, and thus the system as a whole may provide high selectivity/probability of detection with low false alarm rates.

As mentioned previously, it may be desirable to implement an autofocus system with the telescope optics to enable a standoff range of 0.5 m to 10 m for the Raman detection system of the present invention. However, because of the limited space on the robotic arm, the limited amount of weight that can be added to the robot arm 425, and the overall UGV in general, it is desirable to have a compact yet capable focusing apparatus with sufficient fidelity to provide a range of operation over the entire 0.5 to 10 m.

More specifically, depth of focus of an optical system is proportional to the square of the of the collection optics F/#. When target distance varies—due to operator motion or target height variations—to maintain good focus over the full range of target distances, F/# has to be large. However, collected light is inversely proportional to the square of the F/#. Thus, there is a fundamental incompatibility between the need for large F/# to provide large depth of focus and the need for small F/# to allow collection of more Raman scattered light.

However, implementing an autofocus system capable of maintaining precise focus as target distance varies, the need for large depth of focus—and hence large F/#—goes away. Small F/# collection optics can now be used that collect more Raman scatter, giving a corresponding increase in overall Raman sensor system S/N ratio.

Figure 6:
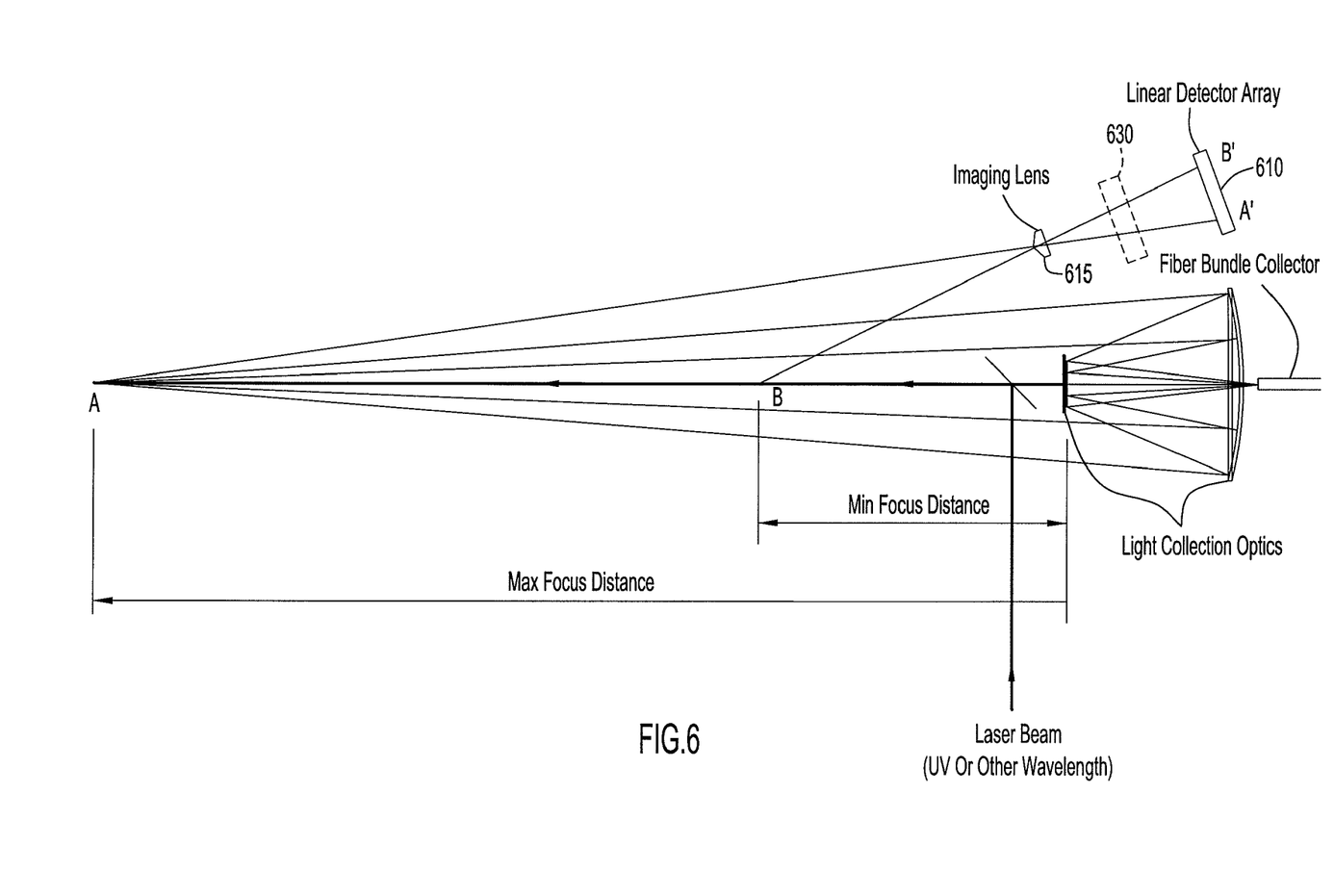
FIG. 6 depicts an autofocus system in accordance with the present invention.

In accordance with an embodiment of the present invention, and with reference to FIG. 6, a primary minor of the telescope optics is configured to move on a translation stage (not shown) that enables precise focus for all target distances in the range of interest.

Target distance is assessed by use of a small lens (perhaps just a few mm in diameter) that images the UV laser beam spot at the target onto a linear detector array 610. (Any other co-aligned laser beam at any other wavelength could also be used.) Because the lens lies off the axis of the collection optics, parallax comes into play. Target distance is mapped by the location of the image spot on the linear array 610. In FIG. 6, as target distance varies over the range, A-B, the image spot on the linear array ranges between A' and B'. The focal length of the imaging lens 615 would generally be chosen so that the range A'-B' covers a significant portion of the array width.

Image spot location on the linear array is simply determined by the pixel that receives the largest signal. A centroiding algorithm may be implemented to increase the precision of the target distance measurement. To allow continuous mapping of spot image pixel coordinates to target distance, a calibration procedure is preferably first executed. In the procedure, the system is manually brought to best focus at several different target distances (typically between 3 m and 6 m), spread out over the range of interest. For each target distance, two quantities are noted: the coordinate of the brightest pixel on the linear array 610, and the position encoder reading on the translation stage. An equation is then developed that provides a general mapping between pixel coordinate and corresponding target distance.

The mapping equation might typically be a polynomial equation, but many other formulations can also be used. Depending on how accurately focus is required over the target distance range, the equation could be 2nd-, 3rd-, or higher-order.

In one embodiment, the primary minor was attached to a linear translation stage fitted with position encoder. A 2nd-order polynomial equation was generated relating pixel coordinate to a corresponding encoder count number. The target distance sampling rate, and the speed of the processor chip that evaluates the focusing polynomial must both be fast enough to support the desired focus response rate. As an example, sampling may be performed at 250 to 400 Hz.

The F/# of the imaging lens can be adjusted so that highly-reflective surfaces cause near-saturation of the detector. Darker surfaces, such as black asphalt, produce smaller signals. To allow the spot to focus precisely over the entire linear array 610, the array is preferably tilted at an angle known as the Scheimpflug angle. For the arrangement shown in FIG. 6, the Scheimpflug angle is the tilt angle of the linear array 610 that gives best spot focus for all locations in the skewed target plane containing the points A and B. Generally, the Scheimpflug angle in image space is given by target plane tilt angle divided by the lens magnification.

There may be benefit, however, in tilting the linear array 610 at an angle different from the Scheimpflug angle. At such an angle, the image spot on the linear array 610 can be focused for large target distances and out of focus for smaller target distances. By this means, the irradiance falling on a pixel on the linear array 610 can have a much flatter dependence on target distance compared to the inverse square variation that would be normally be expected. With this scheme, a much larger portion of the dynamic range of the linear array can then be allocated to target reflectivity variations rather than target distance variations.

To further increase target reflectivity range that can be accommodated, a filter 630 could be placed in front of the linear array to reduce the amount of light received from highly-reflective targets. The filter could then be removed when the target reflectivity is much smaller. The decision as to when to use the filter could be made by comparing peak signal on the linear array to some reference level. Target reflectivity accommodation range could also be increased by using a second laser (perhaps a visible laser diode) as the focusing reference. This laser could be run at reduced power when target reflectivity is high, and at increased power for lower reflectivity. By departing from the Scheimpflug condition, and by use of filters and/or by varying the laser power in the ways just described, a very large target reflectivity range could be accommodated.

In an actual implementation of the instant embodiment, a weak cylindrical lens was used just in front of the imaging lens. (It could equally be placed just behind the imaging lens.) This produced a line image rather than a spot image on the linear array (whose dimensions are typically 10 μm×10,000 μm). The line image oriented at right angles to the array length. Whereas the cylindrical lens causes no degradation to position resolution obtained from the linear array, it allows the alignment tolerance of the linear array with respect to the line of travel of the image spot to be relaxed significantly, typically by an order of magnitude.

In another embodiment, a linear actuator motor (with built-in position encoder) was used to drive the secondary mirror. The motor was small enough to fit within the footprint of the secondary minor to avoid additional light blocking. Because the secondary mirror might typically be one or two orders of magnitude lighter than the primary mirror, actuation rates can be greatly increased, leading to faster focus response.

Use of an autofocus system like that described herein has several advantages. For example, it removes the system operator of the stressful manual task of having to continually adjust focus while scanning targets. Also, very large target distance ranges (typically 0.1 m to 3 m and even up to 10 m) can be accommodated easily and without operator stress.

Further, by having an autofocus system that provides much more precise focus than obtained manually, the intrinsic depth of focus of the Raman scatter collection optic can be greatly reduced (typically to +/−1 mm). This allows much smaller target distances to be used where F/# of the collection optic is now much smaller and collected Raman scatter is much larger. Large increases in S/N are made possible with corresponding increases in system detection sensitivity and reliability.

Further still, by enabling more Raman scatter to be collected, scan rates of the target area can be increased while maintaining the same signal collection. For instance, a 10× increase in collected Raman scatter enables a proportional scan rate increase for the same delivered signal to the detector. This leads to a proportional reduction in total time to scan a given target area.

Furthermore, with precise autofocus, residual aberrations due to defocus use up much less of an optics aberration budget. As a result, it may be possible to reduce dependence on relatively more sophisticated (and expensive) optics such as aspheric lenses, etc.

Also, autofocus allows the laser spot at the target to be precisely imaged into the center of the collection fiber bundle. This allows fiber bundle diameter to be reduced with a corresponding reduction in the number of fibers in the bundle. (For instance, 37-fiber or 19-fiber bundles may become viable instead of the current 61-fiber bundle that has been used in actual implementations of the system.) This leads to shorter slit lengths whose images now occupy only a subset of the ICCD's detector array, i.e., the detector portion of the ICCD. By only reading out pixels in this subset, detector noise may show a proportional decrease.

As an alternate to the above, magnification of the laser spot on to the collection fiber bundle can be increased, giving a proportionate decrease in image space numerical aperture (NA). This enables use of a smaller NA spectrograph with proportionately smaller diameter optics. To provide the same imaging quality, these optics would be less complicated, and there might even be fewer of them, the end result being less expensive spectrograph optics.

The systems and methods described herein may be embodied in other specific forms without departing from the spirit or essential characteristics thereof. The foregoing embodiments are therefore to be considered in all respects illustrative and not meant to be limiting.

What is claimed is:

1. A system including an unmanned ground vehicle (UGV) having a Raman sensor, the system comprising:
   an unmanned ground vehicle (UGV) having a robot arm;
   a camera mounted on the robot arm;
   a laser and associated telescope mounted on the robot arm in such a way as to point in substantially a same direction in which the camera is pointed, wherein the telescope comprises an autofocus system that includes a lens that is arranged to image a laser beam spot at a target on to a linear detector array and that is positioned to assess target distance based on parallax, wherein the lens and the linear detector array are arranged along a same axis that is off-axis from an axis along which laser light travels to the target and wherein light reflected from the target is passed directly to the lens without intervening reflection;
   a data acquisition and control module mounted on the UGV and configured to receive Raman spectral data from the telescope; and
   a remote base station having a display and a data processing and analysis module that is configured to receive data from the data acquisition and control module.

2. The system of claim 1, wherein the UGV is remotely controlled.

3. The system of claim 1, wherein the UGV operates autonomously.

4. The system of claim 1, further comprising a spectrograph that receives Raman scattered light from the telescope.

5. The system of claim 1, further comprising an umbilical that connects the laser and associated telescope to the data acquisition and control module.

6. The system of claim 1, wherein the base station receives imagery from the camera and displays the same on a display.

7. The system of claim 6, wherein the display is a touch screen display.

8. The system of claim 1, wherein the laser operates at a wavelength of about 262 nm.

9. The system of claim 1, wherein the linear detector array is tilted at an angle consistent with the Scheimpflug angle.

10. The system of claim 1, further comprising a filter arranged in front of the linear detector array.

11. The system of claim 1, wherein the autofocus system provides a depth of focus of +/−1 mm.

12. The system of claim 1, wherein the telescope can be focused to have a stand-off range of about 0.5 m to about 10 m.

13. The system of claim 1, wherein the laser and associated telescope and the data acquisition and control module are modularly configured such that the laser and associated telescope and the data acquisition and control module can be employed by a man-portable Raman sensor.

* * * * *

UNITED STATES PATENT AND TRADEMARK OFFICE
CERTIFICATE OF CORRECTION

| | | |
|---|---|---|
| PATENT NO. | : 8,159,662 B2 | Page 1 of 1 |
| APPLICATION NO. | : 12/235893 | |
| DATED | : April 17, 2012 | |
| INVENTOR(S) | : Rezac et al. | |

It is certified that error appears in the above-identified patent and that said Letters Patent is hereby corrected as shown below:

Column 9, line 56, replace "a primary minor" with -- a primary mirror --;

Column 10, line 23, replace "the primary minor" with -- the primary mirror --; and Column 11, line 15, replace "secondary minor to" with -- secondary mirror to --.

Signed and Sealed this
Third Day of July, 2012

David J. Kappos
*Director of the United States Patent and Trademark Office*